United States Patent [19]

Stuehr et al.

[11] Patent Number: 5,132,407
[45] Date of Patent: Jul. 21, 1992

[54] PURIFIED INDUCIBLE NITRIC OXIDE SYNTHASE FLAVOPROTEIN

[75] Inventors: Dennis J. Stuehr, Lakewood, Ohio; Carl F. Nathan, Larchmont, N.Y.

[73] Assignee: Cornell Research Foundation, Inc., Ithaca, N.Y.

[21] Appl. No.: 765,875

[22] Filed: Sep. 26, 1991

[51] Int. Cl.$^5$ .................... C07K 15/06; C12N 9/00; C12N 9/48; C12N 9/64
[52] U.S. Cl. .................. 530/395; 435/195; 435/212; 435/226; 435/228; 530/397
[58] Field of Search ............... 530/395, 397; 435/195, 435/212, 226, 228

[56] References Cited

PUBLICATIONS

Sakuma et al, Proc. Natl. Acad. Sci. USA 85:8664–8667, 1988.
Iyengar, R., et al Proc. Natl. Acad. Sci, USA, vol. 84, 6369–6373 (Sep. 1987).
Gross, S. S., et al, Biochem. Biophys. Res. Comm., 170, No. 1, 96–103 (Jul. 1990).
Kwon, N. S., et al, J. Biol. Chem. 264, No. 34, 20496–20501 (Dec. 1989).
Kwon, N. S., et al, J. Biol. Chem. 265, No. 23, 13442–13445 (Aug. 1990).
Moncada, S., et al, Biochem Pharmacol, 38, No. 11, 1709–1715 (1989).
Nathan, Carl F., et al, J. Natl. Cancer Inst., 82, No. 9, editorial (May 1990).
Stuehr, D. J. et al, Proc. Natl. Acad. Sci. USA, 82, pp. 7738–7742 (Nov. 1985).
Stuehr, D. J., et al, The Journal of Immunology, 139, No. 2,518–525 (Jul. 1987).
Stuehr, D. J., et al, J. Exp. Med., 169, 1011–1020 (Mar. 1989).
Stuehr, D. J., et al, J. Exp. Med., 169, 1543–1555 (May 1989).
Stuehr, D. J., et al, Biochem. Biophys. Res. Comm., 161, No. 2, 420–426 (Jun. 1989).
Stuehr, D. J., et al. Endothelium-Derived Relaxing Factors (Rubanyi, G. M., et al, eds.), 75–84, S. Karger, Basel, Switzerland, 1990.
Stuehr, D. J., et al, Biochem. Biophys. Res. Comm., 168, No. 2, 558–565 (Apr. 1990).
Stuehr, D. J., et al, The FASEB Journal, vol. 5, 98–103 (Jan. 1991).
Stuehr, D. J., et al, J. Biol. Chem, 266, No. 10, 6259–6263 (Apr. 1991).
Stuehr, D. J., et al, Proc. Natl. Acad. Sci. U.S.A., 88, 7773–7777 (Sep. 1991).
Billiar, T. R., et al, J. Exp. Med., 169, 1467–1472 (Apr. 1989).
Billiar, T. R., et al, Surgery, 106, No. 2, 364–372 (Aug. 1989).
Bredt, D.S., et al, Proc. Natl. Acad. Sci. USA, 87, 682–685 (Jan. 1990).
Curran, R.D., et al, J. Exp. Med., 170, 1769–1774 (Nov. 1989).
Ding, A. H., et al, The Journal of Immunology, 141, No. 7, 2407–2412 (Oct. 1988).
Ding, A. H., et al, The Journal of Immunology, 145, No. 3, 940–944 (Aug. 1990).
Yui, Y., et al, The Journal of Biological Chemistry, vol. 266, No. 19, 12544–12547 (Jul. 5, 1991).
Drapier, J. C., et al, J. Immunol. 140, 2829–2838 (1988).
Mayer B., et al, FEBS Lett., 277, 215–219 (1991).
Schmidt, H. H. H. W., et al, Proc. Natl. Acad. Sci. USA 88, 365–369 (1991).
Tayeh, M. A., et al. J. Biol. Chem. 264, 19654–19658 (1989).
Yui, Y., et al, J. Biol. Chem. 266, 3369–3371 (1991).

Primary Examiner—Howard E. Schain

[57] ABSTRACT

Inducible nitric oxide (NO) synthase flavoprotein purified to an activity more than 400-fold from activated mouse macrophage cell line is water soluble, has a denatured molecular mass as determined by sodium dodecyl sulfate polyacrylamide gel electrophoresis under reducing conditions ranging from 125 to 135 kDa, has a molecular mass in catalytically active form of about 250 kDa, does not require added calcium ions or calmodulin for activity, and on heat denaturation releases flavin adenine dinucleotide in an amount of 1.1±0.1 mol per mol of 130 kDa polypeptide subunit of the purified flavoprotein and flavin mononucleotide in an amount of at least 0.55±0.04 mol per mol of 130 kDa polypeptide subunit of the purified flavoprotein.

3 Claims, 6 Drawing Sheets

PURIFIED INDUCIBLE NITRIC OXIDE SYNTHASE FLAVOPROTEIN

This invention was made at least in part with Government support under National Institutes of Health Grants CA43610 and CA53914; the Government has certain rights in the invention.

TECHNICAL FIELD

This invention is directed at purified inducible nitric oxide (NO) synthase flavoprotein which on heat denaturation releases flavin adenine dinucleotide and also flavin mononucleotide.

BACKGROUND OF THE INVENTION

For several decades nitroglycerin has been administered to humans as a vasodilating agent in the treatment of cardiovascular disease. Recently, it has been shown that nitroglycerin so administered is converted in the body to nitric oxide which is the pharmacologically active metabolite. Still more recently, nitric oxide has been shown to be formed enzymatically from arginine as a normal metabolite which is an important component of endothelium-derived relaxing factors (EDRFs). EDRFs are currently being intensively studied as participating in regulation of blood flow and vascular resistance. In addition to vascular endothelium, macrophages have also been shown to produce nitric oxide in the body which is a component of their cell killing and/or cytostatic function.

More recently it has been established that the enzyme forming nitric oxide from arginine, i.e., nitric oxide synthase, occurs in two distinct forms, namely the constitutive form and the inducible form. The constitutive form is present in normal endothelial cells, neurons and some other tissues. Formation of nitric oxide by the constitutive form in endothelial cells is thought to play a role in normal blood pressure regulation. The inducible form of nitric oxide synthase has been found to be present in activated macrophages and is induced in endothelial cells and vascular smooth muscle cells, for example, by various cytokines and/or microbial products. It is thought that, in sepsis or cytokine-induced shock, overproduction of nitric oxide by the inducible form of nitric oxide synthase plays an important role in the observed life-threatening hypotension.

Considerable research effort has been expended to characterize the constitutive and inducible forms.

Thus far the constitutive form has been purified to homogeneity from rat and porcine cerebellum and rat neutrophils. Said purified constitutive form is reported to have a molecular mass as determined by sodium dodecyl sulfate polyacrylamide gel electrophoresis ranging from 150 kDa to 160 kDa, to appear to be a monomer, to require calcium and a calcium-binding protein such as calmodulin for its activation, and to be unstable (that isolated from rat cerebellum is reported to lose 50% of its enzyme activity when stored at 0° C. for 2 hours). See Bredt, D. S., et al, Proc. Natl. Acad. Sci. USA, 87, 682-683 (1990); Mayer, B., et al, FEBS Lett., 277, 215-219 (1991); Schmidt, H. H. H. W., et al, Proced. Natl. Acad. Sci., USA 88, 365-369 (1991); Yui, Y, et al, J. Biol. Chem. 266, 3369-3371 (1991).

The induction of inducible form nitric oxide synthase activity from mouse macrophage cell line by exposure various cytokines and/or microbial products is reported in D. J., et al, J. Immunol. 139, 518-525 (1987); Drapier, J. C., et al, J. Immunol. 140, 2829-2838 (1988); and Ding. A. H., et al J. Immunol. 141, 2407-2412 (1988). Partial purification of activated mouse macrophage cell line inducible form nitric oxide synthase activity by affinity chromatography on adenosine 2', 5'-bisphosphate (2',5 ADP)-Sepharose resin is reported in Stuehr, D. J., et al, Biochem. Biophys. Res. Comm. Vol. 161, No. 2, 420-426 (6/15/89) and Kwon, S. K., et al, J. Biol. Chem. 264, 2049-20501 (1989) and Stuehr, D. J., et al, Biochem. Biophys. Res. Comm., Vol. 168, No. 2, 558-565 (4/30/90); by this method the inducible form activity is purified about 50-100-fold. For this partially purified inducible form nitric oxide synthase, nitric oxide synthesis was reported to be about 50% dependent on exogenous flavin adenine dinucleotide, about 50% dependent on glutathione, 84% dependent on tetrahydrobiopterin, 95% dependent on NADPH and 98% dependent on L-arginine; see Stuehr, D. J., et al, Biochem. Biophys. Res. Comm. Vol. 168, No. 2, 558-565 (4/30/90). Purification of mouse macrophage cell line inducible form nitric oxide synthase activity 150-200-fold by FPLC anion exchange chromatography on a Mono Q column followed by affinity chromatography on 2',5.-ADP-Sepharose is reported in Stuehr, D. J., et al, J. Biol. Chem. Vol. 266, No. 10, 6259-6263 (4/5/91). Prior to the invention herein, there is no literature report of mouse macrophage cell line inducible form nitric oxide synthase activity having been purified to homogeneity.

SUMMARY OF THE INVENTION

In the present invention, inducible form nitric oxide (NO) synthase has been purified to an activity more than 400-fold from activated mouse macrophage cell line. This inducible form nitric oxide synthase product has been determined to be a flavorprotein and is water soluble. It has been determined to have a molecular mass in catlytically active form of about 250 kDa by size exclusion chromatography. It has been determined by sodium dodecylsulfate plyoacrylamide gel electrophoresis to have a denatured molecular mass ranging from 125 kDa to 135 kDa.

The flavoprotein nitric oxide synthase product, on heat denaturation by boiling for 7 minutes, releases flavin adenine dinucleotide in an amount of $1.1 \pm 0.1$ mol per mol of 130 kDa polypeptide subunit of nitric oxide synthase and flavin mononucleotide in an amount of at least $0.55 \pm 0.04$ mol per mol of 130 kDa polypeptide subunit of nitric oxide synthase product.

The flavoprotein nitric oxide synthase product has a maximal velocity, i.e. a $V_{max}$, of 1.3 $\mu$mol $NO_2$ plus $NO_3$ per min per mg, a $K_m$ for L-arginine of 2.8 $\mu$M, and a $K_m$ for NADPH of about 0.3 $\mu$M.

The flavoprotein nitric oxide synthase product herein as indicated below functions in combination with cofactors to generate NO from L-arginine. The purified nature of the product allows more accurate destinations than when unpurified activated mouse macrophage cell line or less purified activated mouse macrophage cell line is used. It allows, for example, more accurate determination of drugs that will selectively inhibit inducible form, i.e., inhibit inducible form and not constitutive form, so as to obtain drugs useful for treating pathological states associated with inducible NO synthase including septic shock and vascular leak syndrome associated with cytokine therapy, but which will not interfere with the constitutive enzyme homeostatic and regulatory functions in the cardiovascular and nervous systems.

As previously indicated, the flavoprotein nitric oxide synthase product herein is inducible nitric oxide (NO) synthase flavoprotein purified to an activity more than 400-fold. It may sometimes be referred to herein as "purified flavoprotein" or "purified nitric oxide synthase product".

The term "activated mouse macrophage cell line" means mouse macrophage cell line which is catalytically active.

The terms "activity" and "catalytically active" are used herein to mean the characteristic of functioning in combination with cofactor(s) to cause generation of NO from L-arginine. The cofactor(s) include at least NADPH and preferably at least NADPH and tetrahydrobiopterin. Various of the cofactors are recited above in reference to Stuehr, D. J., et al, Biochem. Biophys. Res. Com., Vol. 168, No. 2, 558-565 (4/30/90).

The term "denatured" is used herein to mean flavoprotein which does not function in combination with said cofactor(s) to cause generation of NO from L-arginine.

The term "mol of 130 kDa polypeptde subunit of nitric oxide synthase" is used herein to mean mol of denatured molecular mass of flavoprotein nitric oxide synthase product.

The term "assay conditions" is used herein to mean the following: A 10 μl sample is added to 90 μl of 40 mm Tris.HCl buffer (pH 7.9), containing 4 μM tetrahydrobiopterin, 4 μM flavin adenine dinucleotide, 3 mM dithiothreitol, and 1 mM L-arginine. Then 2 mM of NADPH is added to initiate the reaction. After 1.5 hr at 37° C., residual NADPH is removed enzymatically and nitrite is assayed.

DETAILED DESCRIPTION

The preferred source of mouse macrophage cell line for activation for the starting material for the purified nitric oxide synthase flavoprotein product herein is RAW 264.7 cell line which is available from the American Type Culture Collection, Bethesda, Md. If desired, the cell line for activation for the starting material can be obtained from mouse (e.g. female $CD_1$ mice) peritoneal cavity by washing with appropriate culture medium (e.g. RPMI 1640), recovering the cell pellet (e.g. by centrifugation), suspending the recovered cell pellet in appropriate culture medium (e.g. RPMI 1640 containing 10% heat-inactivated fetal calf serum and 2 mg/100ml of gentamicin sulfate), culturing and recovering cells.

Once the cell line is obtained or prepared, it is readily cultured at 37° C., 5% $CO_2$ in appropriate culture medium, e.g. in Eagle's Medium (α modification) or RPMI 1640, supplemented with L-glutamine, penicillin, streptomycin and 8% bovine calf serum. When the cell density reaches approximately $10^6$ cells per ml, the cultured cell line is ready for activation to induce nitric oxide synthase activity.

The activation is carried out by adding cytokine and/or microbial product inducing agent(s) and culturing for sufficient time to culture activated cells which are harvested and formed into a suspension of activated cells. In a preferred activation method the combination of inducing agents recombinant mouse interferon-gamma (100 units/ml) and Eschericia coli lipopolysaccharide (2 μg/ml) are added and the admixture is maintained for 10-12 hours before harvesting of the activated cells.

Inducible nitric oxide (NO) synthase flavoprotein is then freed from the cells by lysis, e.g. by freeze-thawing in the presence of protease inhibitors, and lysate fraction containing said flavoprotein is recovered, e.g. as the supernatant from centrifugation of the lysate and is readily stored at −80° C.

The purified nitric oxide synthase flavoprotein product herein is obtained from lysate fraction by three successive chromatography steps, a first chromatography step based on charge interaction, a second chromatography step based on substrate specificity and a third chromatography step based on molecular mass.

A suitable buffer for use in each of the chromatography steps is 20 mM-1,3-bis[tris(hydroxymethyl)methylaminopropane (pH 7.2) containing 5 mM L-arginine, 3 mM dithiothreitol, 2 μM flavin adenine dinucleotide, 1 μM tetrahydrobiopterin [(6RS)-2-amino-4-hydroxy -6-(L-erythro-1,2-dihydroxypropyl) -5,6,7,8 -tetrahydropteridine], and 10% (vol/vol) glycerol.

In the chromatography steps, suitable assay conditions are those described above.

In the first of the three chromatography steps, lysate fraction containing induced nitric oxide synthase activity (e.g. supernatant obtained from centrifugation of the lysate as described above) is loaded into a Mono Q anion-exchange column and then elution is carried out utilizing a programmed gradient from 0.12 to 1.0 M NaCl.

In the second of the three chromatography steps, active fractions from the first step are subjected to affinity chromatography on a column containing adenosine 2′, 5′-bisphosphate-Sepharose resin. The active fractions from the first chromatography step are loaded directly into the column. After unbound protein elutes, the non specifically bound proteins are eluted with the aforedescribed buffer containing 0.6 M NaCl. The induced nitric oxide synthase activity is then eluted with buffer containing 8 mM NADPH.

In the third chromatography step, active fraction after concentration and washing (to remove most residual NADPH), is subjected to gel filtration chromatography using column buffer supplemented with 0.2 M NaCl. Purified inducible nitric oxide (NO) synthase flavoprotein as described hereinbefore is recovered.

The invention is illustrated in the following working example.

In the working example, all the chromatography columns were from Pharmacia LKB. The chromatography column for the first chromatography step was a prepacked Mono Q HR 10/10. The chromatography column for the second chromatography step was a 5×100-mm column containing adenosine 2′, 5′-bisphosphate-Sepharose resin. The column for the third chromatography step was a prepacked TSK G3000 SW (7.5×600 mm) column. All chromatography for purification was carried out with the columns at room temperature. Eluant fractions from chromatography were collected into plastic tubes on ice. The buffer for all chromatography steps was 20 mM 1,3-bis[tris(hydroxymethyl)methylamino] propane (pH 7.2) containing 5 mM L-arginine, 3 mM dithiothreitol, 2 µM flavin adenine dinucleotide, 1 µM tetrahydrobiopterin [(6R,S)-2-amino-4-hydroxy-6-(L-erythro-1,2-dihydroxypropyl)-5,6,7,8-tetrahydropteridine), and 10% (vol/vol) glycerol, except where otherwise specified. Assays for nitric oxide synthase activity were carried out under the assay conditions set forth above. In these assays nitrite concentration was measured as follows: Aliquots (50- or 100 µl) were incubated with an equal volume of Griess reagent (1% sulfanilamide/0.1% naphthylethylene diamine dihydrochloride/2.5% $H_3PO_4$) at room temperature for 10 minutes. The absorbance at 550 nm was determined in a Biotek microplate reader. $NO_2$ was determined using sodium nitrite as a standard. Lysed cell-free medium alone contained 0.2 to 0.3 nmol of $NO_2$/well; this value was determined in each experiment and subtracted from the value obtained with the synthase containing sample. Fractions were assayed in duplicate. In some cases, in making kinetic measurements, production of nitrate and nitrite (stable oxidation products of nitric oxide that accumulate quantitatively over time under the conditions used) was monitored by an automated nitrite/nitrate analyzer as described in Green, L. C., et al, Anal. Biochem. 126, 113–138 (1982). Values on activity and other properties are averages from three purifications starting with a mean of $5 \times 10^9$ cells.

EXAMPLE

RAW 264.7 macrophages (American Type Culture Collection, Bethesda, Md.) were grown at 37° C., 5% $CO_2$ in 6 liters of RPMI 1640 (KC Biological Inc., Lenexa, KS) supplemented with 8% bovine calf serum (HyClone Systems, Logan, Utah), L-glutamine (584 mg/l), pencillin (50 U/Ml), and streptomycin (50 µg/ml). When cells reached a density of approximately $10^6$ cells per ml, 100 units/ml of recombinant mouse interferon-gamma (Genentech) and 2 µg/ml of *Escherichia coli* lipopolysaccharide (Sigma Chemical Co., St. Louis, Mo.) were added to induce nitric oxide synthase activity. After 10–12 hr, the cells were harvested by centrifugation at 4° C. and resuspended in 80 ml of ice-cold saline that contained 25 mM glucose. The yield was about $5 \times 10^9$ cells with a viability (by trypan-blue exclusion) of greater than 90%. The cells were repelleted and resuspended in 16 ml of cold $H_2O$ containing protease inhibitors (0.1 mM phenylmethylsulfonylfluoride, 5 µg/ml aprotinin, 1 µg/ml chymostatin, and 5 µg/ml pepstatin A), and then lysed by three cycles of rapid freeze-thawing. The lysate was centrifuged at 100,000 ×g for 90 min. at 4° C. and the supernatant which contained nitric oxide synthase activity was stored at −80° C.

Figure 1:
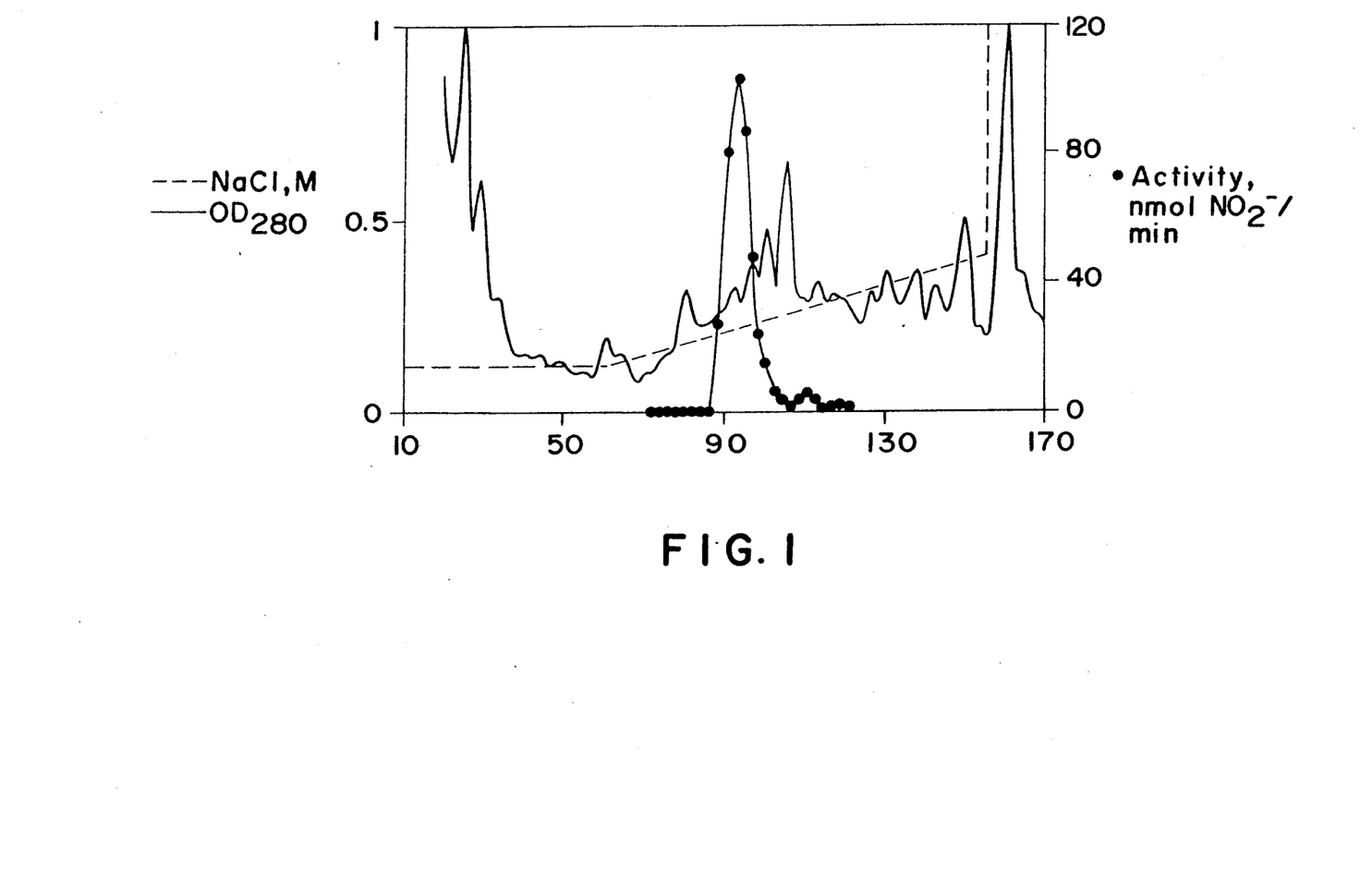
FIG. 1 depicts an elution profile on eluant from the first chromatography step of the purification of the working example.

The supernatant was chromatographed in three runs of 5 ml each on the Mono Q column in a first chromatography step at a flow rate of 2 ml/min. A programmed gradient was run from 0.12 to 1.0 M NaCl to elute nitric oxide synthase activity. An elution profile is depicted in FIG. 1. In FIG. 1, $OD_{280}$ stands for optical density at 280 nm, the dashed line represents the molarity of the NaCl, the solid line without the filled-in circles represents the total protein eluted as determined at $OD_{280}$, and the solid line with filled-in circles represents the fractions with nitric oxide synthase activity with reference to the Y-axis at the right.

Figure 2:
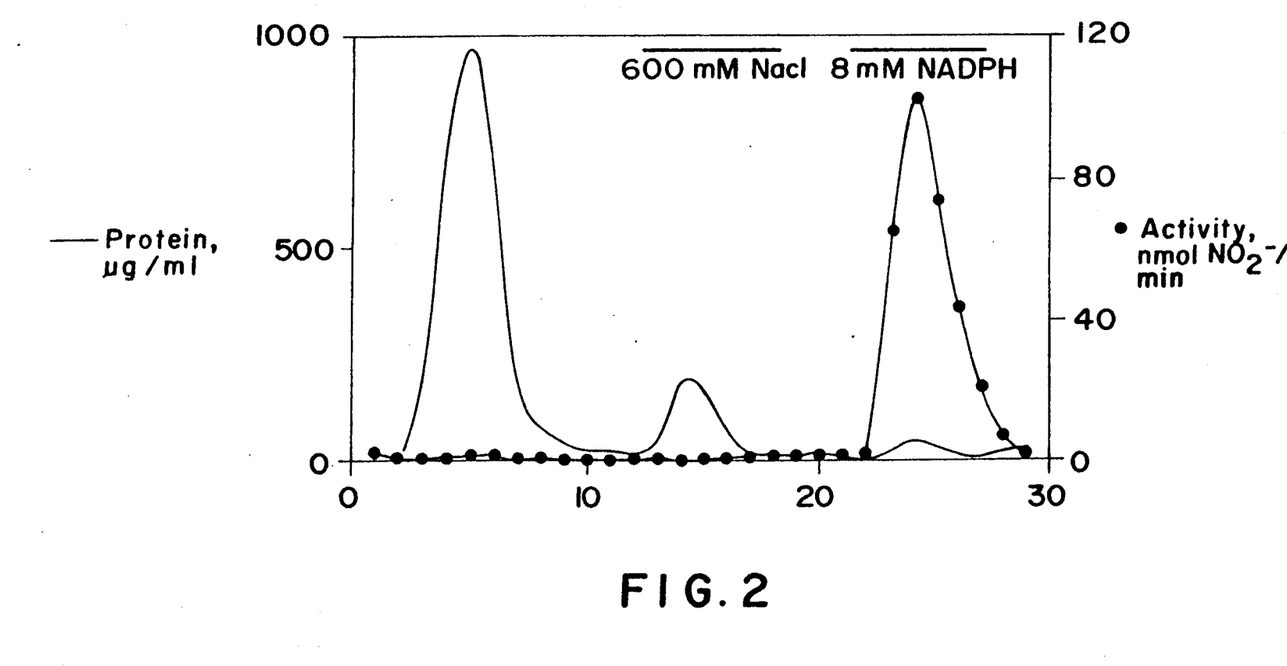
FIG. 2 depicts an elution profile on eluant from the second chromatography step of the purification of the working example.

The active fractions from the first chromatography step (approximately 10 ml each) were respectively used for three runs in a second chromatography step. Each run involved the following. Active fraction from a first chromatography step run was loaded directly at 0.3 ml/min onto the adenosine 2′, 5′-bisphosphate-Sepharose resin affinity column. After unbound protein had been eluted, the nonspecifically bound proteins were eluted with 5 ml of buffer containing 0.6 M NaCl. Nitric oxide synthase activity was then eluted with 5 ml of buffer containing 8 mM NADPH. An elution profile is depicted in FIG. 2. In FIG. 2, the protein eluted is indicated by the solid line with no filled-in circles with reference to the Y-axis at the left and the nitric oxide synthase activity eluted is indicated by the solid line with filled-in circles with reference to the Y-axis at the right.

The active fractions from the three runs of the second chromatography were pooled (15 ml) and concentrated at 4° C. in a Centricon-30 microconcentrator (Amicon). The concentrate (300–400 µl) was washed twice with 1 ml of buffer to remove most of the residual NADPH. The sample (300–400, µl) was stored at −80° C.

Figure 3:
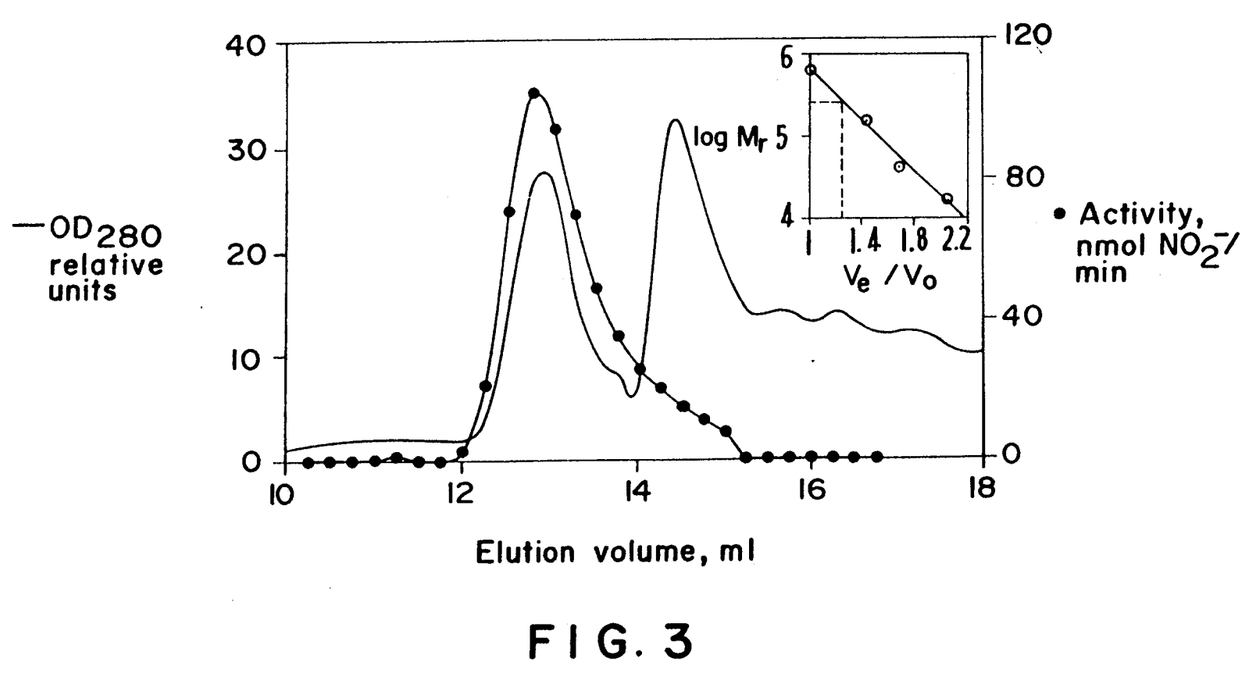
FIG. 3 depicts an elution profile on eluant from the third chromatography step of purification of the working example and includes an inset figure depicting molecular mass determination.

The 300–400 µl sample was subjected to size exclusion gel filtration chromatography on a TSK G3000 SW column. This was carried out at 0.25 ml/min on 50 µl aliquots of the 300–400 µl sample, using column buffer supplemented with 0.2 M NaCl. The elution profile is depicted in FIG. 3. In FIG. 3, $OD_{280}$ stands for optical density at 280 nm, the solid line without filled-in circles represents the total protein eluted with reference to the Y-axis at the left and the solid line with filled-in circles represents nitric oxide synthase activity with reference to the Y-axis at the right, and the inset figure depicts molecular weight determination and $M_r$ stands for relative molecular mass and $V_e/V_o$ is the ratio of volume of elution of the peak in question to the total included volume of the column, and the dashed line represents the nitric oxide synthase active fractions obtained from the gel filtration chromatography and the molecular weight standards for the inset figure are bovine thyroglobulin (670,000), bovine gamma-globulin (158,000), ovalbumin (44,000) and horse myoglobin (17,000). As indicated in FIG. 3, protein was eluted in two peaks with the first peak being nitric oxide synthase. The nitric oxide synthase flavoprotein product from the TSK G3000 SW column, i.e., purified enzyme, was estimated as shown in the inset figure of FIG. 3 to have a molecular mass of about 250 kDa. (This result was confirmed using a TSK G4000 SW (7.5×600 mm) column.) The nitric oxide synthase flavoprotein product was obtained in an amount of approximately 1.5 ml. The purified enzyme could be stored at −80° C.

The amount of protein, the total activity, the specific activity, the yield percent and the purification factor were determined for the various stages to be as follows (values are averages determined on products from three purifications): For lysate supernatant, samples on average contained 198 mg protein, had a total activity of 487.2 nmol of $NO_2$ per minute, had a specific activity of 2.5 nmol of $NO_2$ per minute per mg. of protein, had a yield percent of 100 and had a purification factor of 1. For nitric oxide synthase active fraction obtained from the Mono Q column, fractions on average contained 7.6 mg protein, had a total activity of 141.2 nmol $NO_2$ per minute, had a specific activity of 21.3 nmol $NO_2$ per minute per mg of protein, had a yield percent of 29% and had a purification factor of 9. For nitric oxide synthase active fraction obtained from the 2', 5'-ADP-Sepharose resin column, fractions on average contained 0.27 mg. protein, had a total activity of 50.0 nmol of $NO_2$ per minute, had a specific activity of 197 nmol of $NO_2$ per minute per mg of protein, had a yield percent of 10.2% and had a purification factor of 83. For purified nitric oxide synthase product obtained from the TSK G3000 column, fractions on average contained 0.04 mg protein, had a total activity of 42.4 nmol of $NO_2$ per minute, had a specific activity of 1060 nmol of $NO_2$ per minute per mg of protein, had a yield percent of 8.7 and had a purification factor of 426. Thus the nitric oxide synthase product from the TSK G3000 SW column was purified 426-fold compared to the nitric oxide synthase in the lysate supernatant. The purified nitric oxide synthase product was determined to have a specific activity of 1313 nmol of $NO_2$ plus $NO_3$ per minute per mg of enzyme when assayed in the presence of L-arginine, NADPH, tetrahydrobiopterin, flavin adenine dinucleotide and reduced thiol.

Figure 4:
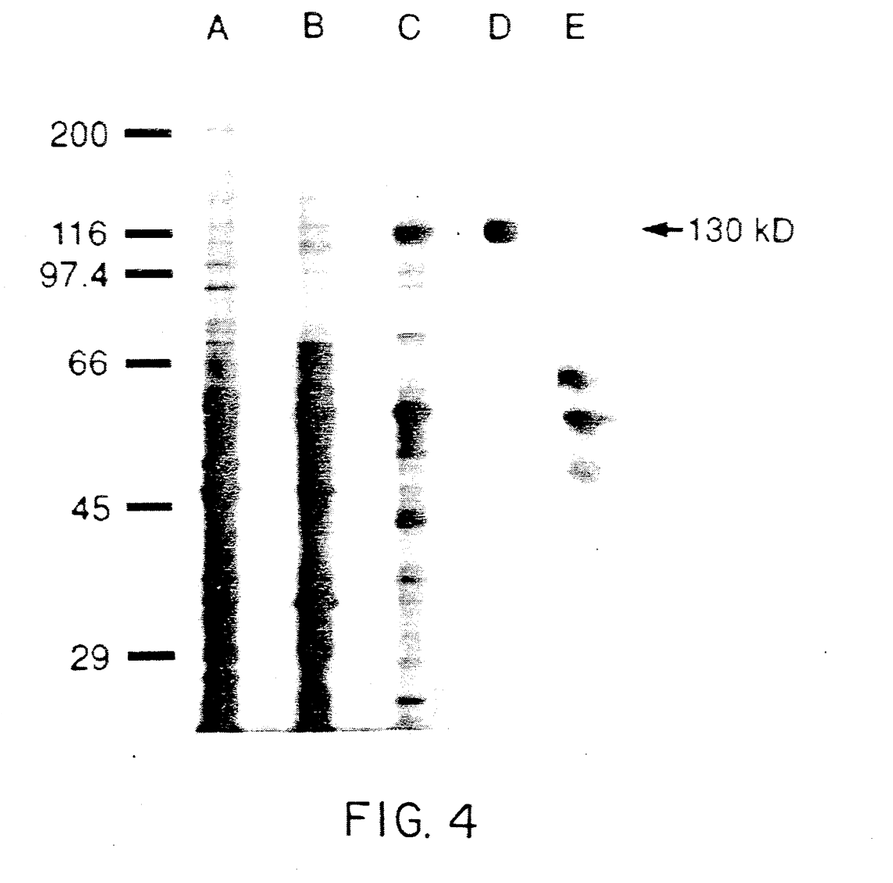
FIG. 4 depicts sodium dodecyl sulfate polyacrylamide gel electrophoresis profiles for various stages of synthase purification and also for partially purified noninduced-macrophage lysate supernatant.

The sodium dodecyl sulfate polyacrylamide gel electrophoresis profile determined for various stages is depicted in FIG. 4 (7.5% polyacrylamide gel, 1 μg of protein per lane, silver-stained). In FIG. 4, lane A represents results for the crude lysate, i.e., the lysate prior to chromatography, lane B represents results for active fraction eluted from the Mono Q column, lane C represents results for active fraction eluted from the 2', 5'-ADP-Sepharose resin column, lane D represents purified nitric oxide synthase product from the TSK G3000 SW column and lane E represents results for non induced RAW 264.7 cell supernatant purified in an identical manner through the Mono Q and 2', 5'-ADP-Sepharose resin steps, and the molecular weight standards indicated are rabbit muscle myosin heavy chain (200,000), E. coli beta-galactosidase (116,000), rabbit muscle phosphorylase b (97,400), bovine albumin (66,000), ovalbumin (45,000) and bovine carbonic anhydrase (29,000). As indicated by good definition of the results depicted in FIG. 4 for lane D, the purified nitric oxide synthase product from the TSK G3000 SW column provides a tight triplet of silver-stained protein bands (i.e. three very closely spaced bands) of estimated molecular mass of 125–135 kDa which has been averaged to 130 kDa. Despite the fact that there is a triplet, the tightness of the bands indicates purification to homogeneity and probably indicates a minor degree of proteolysis that occurs prior to the sodium dodecyl sulfate polyacrylamide gel procedure. The molecular mass obtained is a denatured molecular mass (because boiling the sample in sodium dodecyl sulfate for electrophoresis denatures the protein) and is about half of that estimated for the catalytically active nitric oxide synthase on both TSK G3000 SW (FIG. 3, inset) and TSK G4000 SW gel filtration columns. This suggests that the inducible (macrophage source) nitric oxide synthase product is catalytically active as a dimer. Comparison of the results in lanes D and E in FIG. 4 suggests that the protein band triplet associated with the purified nitric oxide synthase product was induced by interferon-gamma and E. coli lipopolysaccharide on activation of the macrophage cell line therewith.

For purified nitric oxide synthase product from the TSK G3000 SW column on incubation for three hours under standard assay conditions, nitric oxide synthase activity was enhanced less than 20% by added calcium (2 mM) or added calcium (2 mM) plus calmodulin (100 units/ml). In this experiment, the activity determined for no additive was 203±13 nmol of $NO_2$ per minute per mg, the activity determined with calcium as additive was 241±5 nmol of $NO_2$ per min per mg and the activity determined with calcium plus calmodulin as additive was 224±16 nmol of $NO_2$ per min per mg.

Kinetic measurements were taken on the purified nitric oxide synthase product from the TSK G3000 SW column. The initial rate of nitric oxide synthesis was measured spectrophotometrically using the oxyhemoglobin assay for nitric oxide. This method is based on the rapid reaction of nitric oxide with oxyhemoglobin to form methemoglobin and $NO_3$ with an accompanying increase in differential absorbance at 401 nm minus 411 nm. Reactions were carried out in 1 ml of 40 mM Tris buffer, pH 7.9, in cuvettes at 25° C. and started by the addition of substrate. Each reaction contained 20 μg of the nitric oxide synthase preparation. Concentrations of cofactors were as standard, except that NADPH was 200 μM and dithiothreitol was 150 μM. In addition, the reactions contained 0.5 unit of dihydropteridine reductase (to ensure full recycling of tetrahydrobiopterin) and 1.1 μM oxyhemoglobin (prepared by dithionite reduction and subsequent chromatography on a desalting column). Initial rates were linear for at least 3 min. $K_m$ and $V_{max}$ values were derived from Hanes-Woolf plots of v/[S] versus [S]. The $V_{max}$ for the purified nitric oxide synthase product was determined to be 1.3 μmol of $NO_2$ plus $NO_3$ per min per mg. The $K_m$ for L-arginine as substrate was determined to be 2.8 μM and the $K_m$ for NADPH as substrate was determined to be about 0.3 μM.

The purified nitric oxide synthase product from the TSK G3000 SW column could be stored unconcentrated at about 15 μg/ml for at least 6 hr at 4° C. or overnight at −80° C. without loss of activity. Under the aforestated assay conditions, the specific activity of the nitric oxide synthase remained constant with dilution over the protein concentration range tested (0.05–1.3 μg/ml). When the purified nitric oxide synthase product from the TSK G3000 SW column was incubated at 37° C. under assay conditions, the specific activity decreased slowly, falling to 56% of its original value after 6 hours.

The purified nitric oxide synthase product from the TSK G3000 SW column was used to produce a rabbit antiserum. The antiserum labelled the cytoplasm of mouse peritoneal macrophages or RAW 264.7 cells treated with interferon-gamma or E. coli lipopolysaccharide much more strongly than macrophages treated with interferon-gamma alone or E. coli lipopolysaccharide alone. There was no labelling of nonactivated macrophages. Immunoblotting of macrophage lysates yielded comparable results.

Purified nitric oxide synthase product was prepared as described above except that the gel filtration chromatography step was performed in the absence of flavin adenine dinucleotide. A portion of the nitric oxide synthase product (8 μg, 1 ml) was boiled for 7 minutes to release noncovalently bound flavin adenine dinucleotide and flavin mononucleotide, and then the sample was deproteinated by filtration through Centricon-30 microconcentrators and stored on ice. Flavin adenine dinucleotide and flavin mononucleotide in 0.3-ml aliquots of the sample were separated by HPLC on an Applied Biosystems/Brownlee Lab RP-18 reverse-phase column (220×4.6 mm). This was carried out as follows: The conditions at injection were 93% buffer A(5 mM ammonium acetate, pH 6.0)/7% methanol flowing at 1 ml/min. After 2 minutes, a linear gradient was developed over 13 minutes to 70% methanol. Flavin adenine dinucleotide and flavin mononucleotide were detected using a Hitachi S-1000 flow-through fluorometer set at 460 nm for excitation and 530 nm for emission. Under these conditions, authentic flavin adenine dinucleotide (2.4 nmol) and flavin mononucleotide (2.2 nmol) were completely resolved and eluted at 1.2 and 13.1 minutes, respectively. The flavin adenine dinucleotide and flavin mononucleotide in eluant fractions were quantified by measuring peak heights relative to standard curves, which were linear (correlation coefficient, r=0.99) between 0 and 45 pmol of flavin adenine dinucleotide or flavin mononucleotide. The HPLC-purified fluorophores released from the nitric oxide synthase were collected separately and their excitation-emission spectra were obtained using a Spex Industries (Edison, NJ) Fluorolog fluorometer. Spectra obtained were compared with those of authentic flavin adenine dinucleotide and flavin mononucleotide dissolved in the same HPLC buffer.

Figure 5:
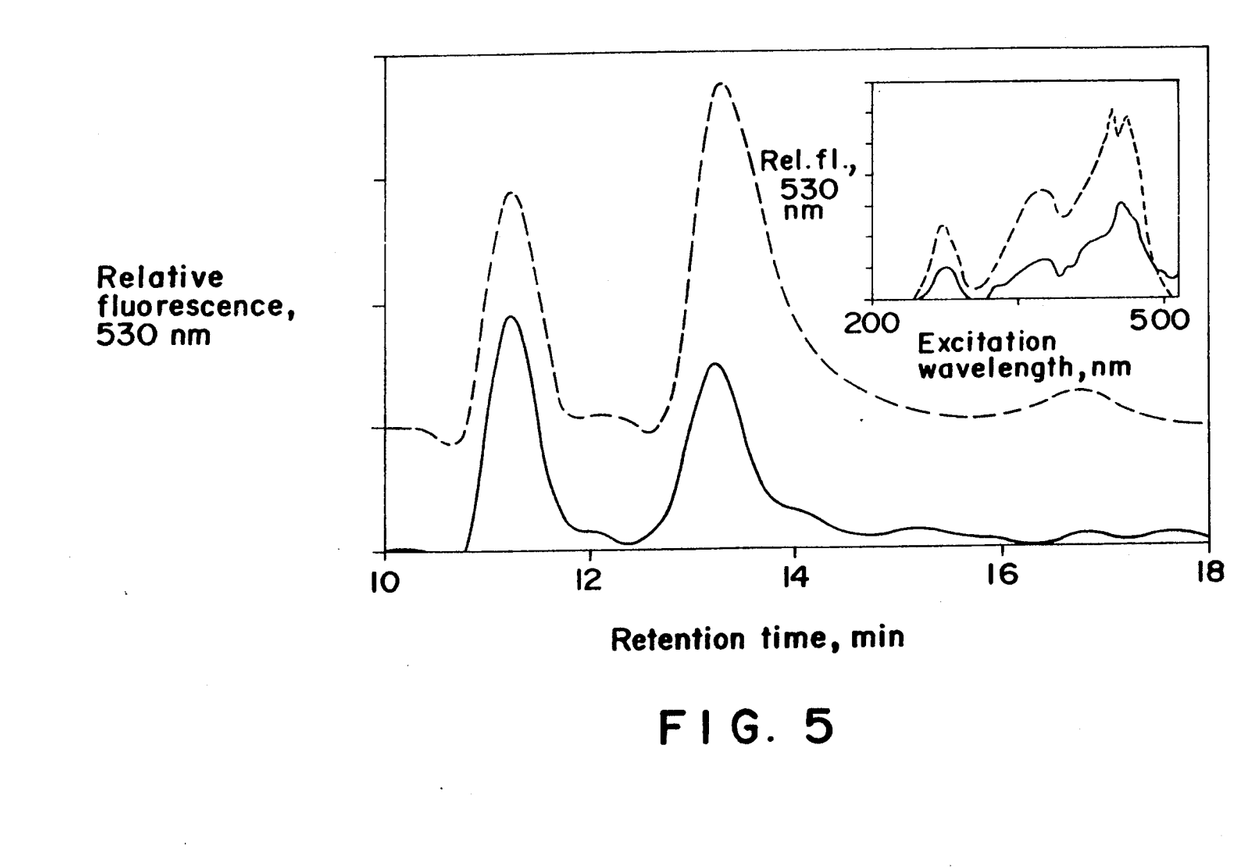
FIG. 5 in its main portion depicts a reverse phase HPLC elution profile on boiled purified product and enables comparison with flavin adenine dinucleotide and flavin mononucleotide standards and in its inset figure provides emission spectrum comparison with authentic flavin mononucleotide.

FIG. 5 in its main portion depicts in a solid line the elution profile for boiled purified nitric oxide synthase product and in a dashed line the elution profile for flavin adenine dinucleotide and flavin mononucleotide standards. Retention times for authentic flavin adenine dinucleotide (2.4 nmol) and authentic flavin monomucleotide (2.2 nmol) were 11.2 and 13.1 minutes, respectively.

The peaks collected from the boiled purified nitric oxide synthase product were determined to have identical excitation maxima and emission maxima to those of authentic flavin adenine dinucleotide and flavin mononucleotide. The inset figure in FIG. 5 depicts the fluorescent emission spectrum of authentic flavin mononucleotide (dashed line) and that of boiled purified nitric oxide synthase product-derived fluorophore eluted at 13 minutes (solid line).

Authentic flavin adenine dinucleotide boiled under the same conditions, i.e. for 7 minutes, was stable and did not generate flavin mononucleotide.

The purified nitric oxide synthase product herein was found to release an average of 1.1±0.1 mol of flavin adenine dinucleotide and 0.55±0.04 mol of flavin mononucleotide per mol of 130 kDa of polypeptide subunit of said nitric oxide synthase. It is speculated that flavin mononucleotide binds less tightly and may be partially lost during the purification procedure; even if this is the case there is at least 0.55±0.04 mol of flavin mononucleotide present per mol of 130 kDa polypeptide subunit of said purified nitric oxide synthase product.

The above indicates that inducible macrophage nitric oxide synthase is a flavoprotein with two molecules of flavin adenine dinucleotide and one molecule of flavin mononucleotide (if the possibility of partial loss mentioned above is ignored) per functional dimer.

Figure 6:
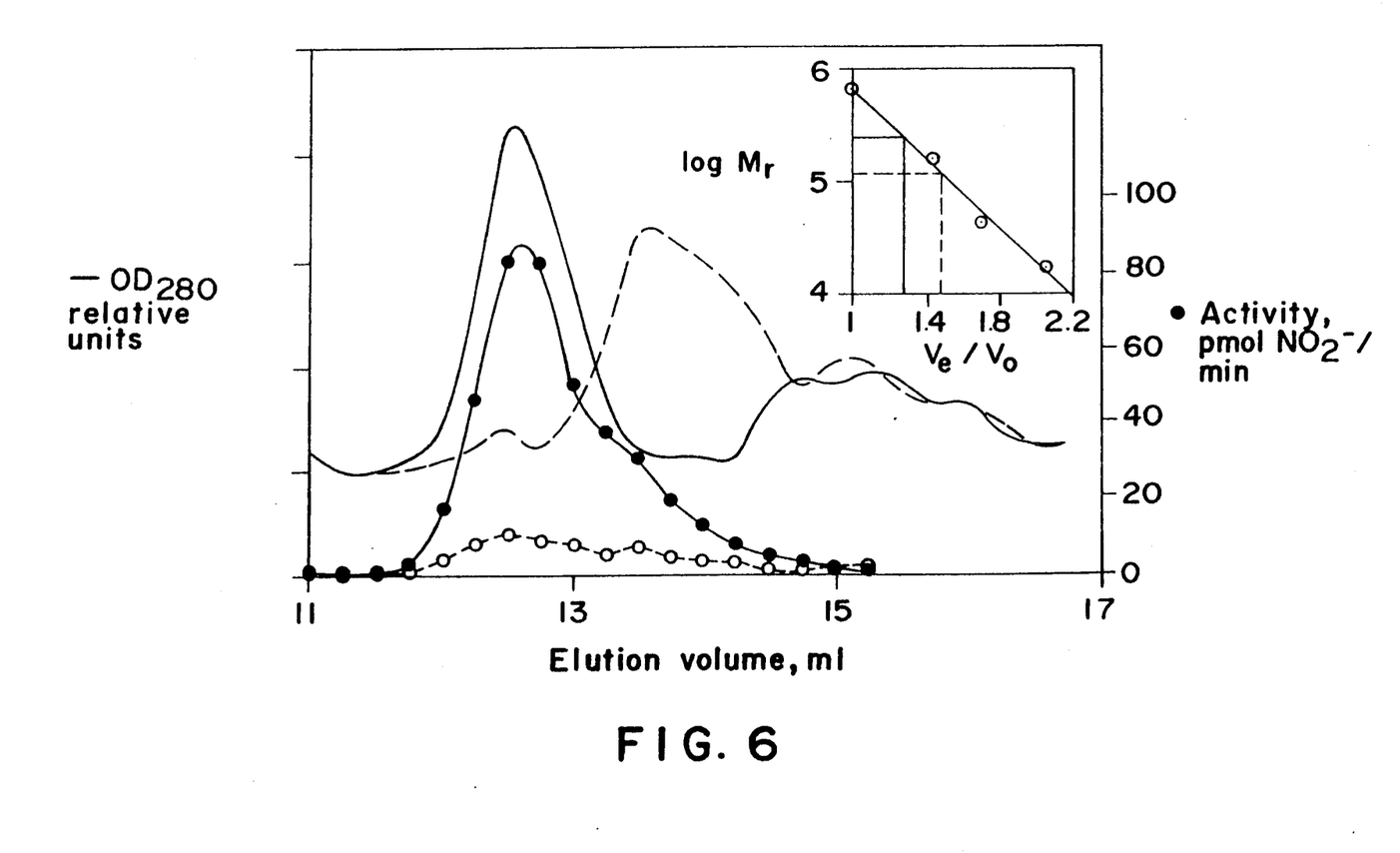
FIG. 6 depicts elution profile where L-arginine was present and was absent in the last chromatography step of purification.

Purification was performed as above except that in one case gel filtration was performed in the absence of L-arginine, tetrahydrobiopterin and flavin adenine dinucleotide, and in another case in the absence of flavin adenine dinucleotide and tetrahydrobiopterin. The results are depicted in the main figure of FIG. 6 where OD stands for optical density at 280 nm, the dashed line with no circles represents protein eluted with reference to $OD_{280}$ in the case where L-arginine was absent, the dashed line with open circles represents nitric oxide synthase activity in the case where L-arginine was absent, the solid line with no circles represents protein eluted with reference to $OD_{280}$ in the case where L-arginine was present, and the solid line with filled circles represents nitric oxide synthase activity in the case where L-arginine was present. As depicted the recovery of nitric oxide synthase activity fell to 15% in the case where L-arginine was absent but was normal (i.e., as indicated in FIG. 3) in the case where L-arginine was present. The inset figure in FIG. 6 wherein $M_r$ stands for relative molecular mass and $V_e/V_o$ is the ratio of the volume of elution of the peak in question to the total included volume of the column, depicts retention time versus molecular mass for the case where the L-arginine was absent (dashed line) and the case where the L-arginine is present (solid line). As depicted in said inset figure, the retention time of the nitric oxide synthase protein peak increased such that its estimated molecular mass decreased from 250 kDa to 121 kDa in the case where L-arginine is absent whereas the retention time indicated an estimated molecular mass of 250 kDa (consistent with FIG. 3) in the case where L-arginine was present. Sodium dodecyl sulfate polyacrylamide gel electrophoresis showed 125-135 kDa proteins eluted in the fractions corresponding to the lower molecular mass. The results suggest that ether L-arginine alone or a combination of flavin adenine dinucleotide and tetrahydrobiopterin is sufficient to maintain the enzyme in its larger, active form and that the induced nitric oxide synthase can be dissociated into inactive monomers in the absence of L-arginine.

Variations in the invention will be obvious to those skilled in the art. Therefore, the invention is defined by the claims.

WHAT IS CLAIMED IS:

1. Inducible nitric oxide (NO) synthase flavoprotein purified to an activity more than 400-fold from activated mouse macrophage cell line, said flavoprotein being water soluble, having a denatured molecular mass as determined by sodium dodecyl sulfate polyacrylamide gel electrophoresis under reducing conditions ranging from 125 to 135 kDa, having a molecular mass in catalytically active form of about 250 kDa, and not requiring added calcium ions or calmodulin for activity.

2. The purified flavoprotein of claim which, on heat denaturation, releases flavin adenine dinucleotide in an amount of 1.1±0.1 mol per mol of 130 kDa polypeptide subunit of purified flavoprotein and flavin mononucleotide in an amount of at least 0.55±0.04 mol per mol of 130 kDa polypeptide subunit of purified flavoprotein.

3. The purified flavoprotein of claim 2 having a $V_{max}$ of 1.3 μmol $NO_2$ plus $NO_3$ per min per mg, a $K_m$ for L-arginine of 2.8 μM and a $K_m$ for NADPH of about 0.3 μM.

* * * * *

UNITED STATES PATENT AND TRADEMARK OFFICE
CERTIFICATE OF CORRECTION

PATENT NO. : 5,132,407

DATED : July 21, 1992

INVENTOR(S) : DENNIS J. STUEHR and CARL F. NATHAN

It is certified that error appears in the above-identified patent and that said Letters Patent is hereby corrected as shown below:

Claim 2 (column 10, line 58), after "claim" insert --1--.

Claim 3 (column 10, line 65), change "$NO_2$ plus $NO_3$" to --$NO_2^-$ plus $NO_3^-$--.

Signed and Sealed this

Twenty-fourth Day of August, 1993

Attest:

BRUCE LEHMAN

*Attesting Officer*    *Commissioner of Patents and Trademarks*